(12) United States Patent
Ranade et al.

(10) Patent No.: US 8,999,307 B2
(45) Date of Patent: Apr. 7, 2015

(54) COMPOSITIONS FOR IMPARTING SUPERHYDROPHOBICITY

(75) Inventors: Rahul A. Ranade, Emerson, NJ (US); Mark S. Garrison, Suffern, NY (US); Freda E. Robinson, Nyack, NY (US); Giovana A. Sandstrom, Saddle Brook, NJ (US)

(73) Assignee: Avon Products, Inc., New York, NY (US)

( * ) Notice: Subject to any disclaimer, the term of this patent is extended or adjusted under 35 U.S.C. 154(b) by 293 days.

(21) Appl. No.: 12/992,729

(22) PCT Filed: Apr. 14, 2009

(86) PCT No.: PCT/US2009/040496
§ 371 (c)(1),
(2), (4) Date: Nov. 15, 2010

(87) PCT Pub. No.: WO2009/140008
PCT Pub. Date: Nov. 19, 2009

(65) Prior Publication Data
US 2011/0070180 A1 Mar. 24, 2011

Related U.S. Application Data

(60) Provisional application No. 61/053,871, filed on May 16, 2008.

(51) Int. Cl.
| | |
|---|---|
| *A61Q 5/06* | (2006.01) |
| *A61K 8/11* | (2006.01) |
| *A61K 8/25* | (2006.01) |
| *A61K 8/26* | (2006.01) |
| *A61K 8/27* | (2006.01) |
| *A61K 8/28* | (2006.01) |
| *A61K 8/29* | (2006.01) |
| *A61K 8/44* | (2006.01) |
| *A61K 8/81* | (2006.01) |
| *A61K 8/897* | (2006.01) |

(52) U.S. Cl.
CPC ... *A61K 8/11* (2013.01); *A61K 8/25* (2013.01); *A61K 8/26* (2013.01); *A61K 8/27* (2013.01); *A61K 8/28* (2013.01); *A61K 8/29* (2013.01); *A61K 8/44* (2013.01); *A61K 8/8123* (2013.01); *A61K 8/8152* (2013.01); *A61K 8/897* (2013.01); *A61Q 5/06* (2013.01); *A61K 2800/412* (2013.01); *A61K 2800/31* (2013.01)

(58) Field of Classification Search
None
See application file for complete search history.

(56) References Cited

U.S. PATENT DOCUMENTS

| | | |
|---|---|---|
| 4,102,703 A | 7/1978 | Tully |
| 5,132,443 A | 7/1992 | Traver et al. |
| 5,500,216 A | 3/1996 | Julian et al. |
| 6,683,126 B2 | 1/2004 | Keller et al. |
| 6,746,833 B2 | 6/2004 | Li et al. |
| 6,800,354 B2 | 10/2004 | Baumann et al. |
| 6,852,389 B2 | 2/2005 | Nun et al. |
| 6,946,170 B2 | 9/2005 | Gerber et al. |
| 7,056,845 B2 | 6/2006 | Waeber et al. |
| 2004/0116591 A1 | 6/2004 | Chen |
| 2004/0186030 A1 | 9/2004 | Hofrichter et al. |
| 2004/0202627 A1 | 10/2004 | Kuroda et al. |
| 2005/0118121 A1 | 6/2005 | Kuroda |
| 2005/0163813 A1* | 7/2005 | Kosbach et al. ............. 424/401 |
| 2005/0201961 A1* | 9/2005 | Lu et al. .......................... 424/63 |
| 2005/0220741 A1 | 10/2005 | Dumousseaux |
| 2006/0222610 A1 | 10/2006 | Elliott |
| 2006/0222615 A1* | 10/2006 | Kuroda et al. ............. 424/70.12 |
| 2006/0257346 A1* | 11/2006 | Mohammadi et al. ...... 424/70.12 |
| 2007/0020208 A1* | 1/2007 | Gutkowski et al. ............ 424/63 |
| 2007/0020220 A1 | 1/2007 | Osborne |
| 2007/0248633 A1 | 10/2007 | Baldo |
| 2008/0063613 A1 | 3/2008 | Cockerell et al. |
| 2009/0130217 A1 | 5/2009 | Roesch et al. |
| 2010/0266648 A1 | 10/2010 | Ranade et al. |
| 2011/0008401 A1 | 1/2011 | Ranade et al. |

FOREIGN PATENT DOCUMENTS

JP H07-187959 7/1995

* cited by examiner

*Primary Examiner* — Jyothsna Venkat
(74) *Attorney, Agent, or Firm* — David M. Joyal; Joan M. McGillycuddy

(57) ABSTRACT

Compositions and methods are disclosed for imparting water repellency to the hair. The compositions generally comprise a first hydrophobic particulate material having a coefficient of dynamic friction of 0.5 or greater in combination with a second hydrophobic particulate material having a coefficient of dynamic friction less than 0.5.

28 Claims, No Drawings

COMPOSITIONS FOR IMPARTING SUPERHYDROPHOBICITY

FIELD OF INVENTION

The present invention relates to methods and compositions for imparting a hydrophobic film on keratin fibers, including hair. More specifically, the invention relates to methods and compositions for forming a super-hydrophobic film on hair.

BACKGROUND OF THE INVENTION

The leaf of the lotus plant exhibits remarkable water-repellency and self-cleaning properties. Although lotus plants prefer to grow in muddy rivers and lakes, the leaves and flowers remain clean and are essentially non-wettable. The lotus plant achieves this effect by producing leaves and flowers with extremely hydrophobic surfaces. When the leaves come in contact with water, the water droplets contract into substantially spherical beads which roll off the surface, sweeping away any particles of dirt they encounter.

On extremely hydrophilic surfaces, a water droplet will completely spread and provide an effective contact angle of essentially 0°. This occurs for surfaces that have a large affinity for water, including materials that absorb water. On many hydrophilic surfaces, water droplets will exhibit contact angles of about 10° to about 30°. In contrast, on hydrophobic surfaces, which are incompatible with water, larger contact angles are observed, typically in the range of about 70° to about 90° and above. Some very hydrophobic materials, for example, Teflon™, which is widely regarded as a benchmark of hydrophobic surfaces, provides a contact angle with water of as high as 120°-130°.

Against this background, it is remarkable that the lotus leaf can produce a contact angle with water of about 160°, which is substantially more hydrophobic than Teflon™. The lotus leaf is thus an example of a "super-hydrophobic" surface. For the present purposes, a super-hydrophobic surface may be said to be one which provides a contact angle with water of greater than about 140°. This effect is believed to arise due to the three-dimensional surface structure of the leaf wherein wax crystals self-organize to provide roughness on a nano- or micro-meter scale. The hydrophobic surface protuberances reduce the effective surface contact area with water and thus prevent adhesion and spreading of the water over the leaf.

The discovery of the aforementioned properties of the lotus leaf and elucidation of its mechanism has led to a variety of engineered super-hydrophobic surfaces. Such super-hydrophobic surfaces have water contact angles ranging from 140° to nearly 180°. Such surfaces are extremely difficult to wet. On these surfaces, water droplets simply rest on the surface, without actually wetting to any significant extent. Superhydrophobic surfaces have been obtained in a variety of ways. Some of these very hydrophobic materials are found in nature. Other superhydrophobic materials are made synthetically, sometimes as mimics of natural materials.

U.S. Pat. No. 6,683,126 describes a coating composition for producing difficult to wet surfaces comprising a finely divided powder, where the particles are porous and have a hydrophobic surface, combined with a film forming binder such that the ratio of the powder to the binder is 1:4.

U.S. Pat. No. 6,852,389 describes the process of production of superhydrophobic materials for self cleaning applications.

U.S. Pat. No. 6,946,170 describes a self cleaning display device.

U.S. Pat. No. 7,056,845 describes a method for the application of a finishing layer which is water repellant for use in finishing of textiles, fabrics and tissues.

U.S. Pat. No. 6,800,354 describes process of production of self cleaning substrates of glass, ceramic, and plastics.

U.S. Pat. No. 5,500,216 describes a method of reducing drag through water by applying a film of rough particles of hydrophobic metal oxides where the particles have a distribution of two different size ranges.

While hydrophobic or super-hydrophobic materials have been described above, there remains a need for hydrophobic or super-hydrophobic materials in hair care compositions which impart hydrophobic films, particularly superhydrophobic films, on hair fibers. The compositions described in the foregoing patents are not suitable for forming a superhydrophobic film on hair because the tactile and aesthetic attributes of such films are not acceptable. In particular, commonly employed particulates in superhydrophobic films, such as hydrophobically-modified silica or alumina, impart a chalky feeling when applied to the hair and produce a white appearance and reduction in shine.

It is therefore an object of the invention to provide cosmetic compositions for application to hair (keratin) fibers which form a super-hydrophobic film thereon. It is a further object of the invention to provide methods for imparting superhydrophobic films on hair to achieve water-resistant, self-cleaning and/or long-wear properties. If is also an object of the invention to provide superhydrophobic films on hair which have consumer-acceptable aesthetics, including feel, color, and shine.

SUMMARY OF THE INVENTION

In accordance with the foregoing objectives and others, the present invention provides compositions and methods for forming super-hydrophobic films on a surface, preferably a biological integument, and more preferably a keratin fiber (hair).

In one aspect of the invention, compositions for rendering a keratin fiber water-repellant (and preferably superhydrophobic) are provided comprising: (a) from 0.1 to 5% by weight, and more typically 0.75% to about 3% by weight, of a first hydrophobic particulate material, the first hydrophobic particulate material having a coefficient of dynamic friction of 0.5 or greater; (b) from 0.1 to 5% by weight of a second hydrophobic particulate material, the second hydrophobic particulate material having a coefficient of dynamic friction less than 0.5; and (c) from 90 to 99.8% by weight of a volatile solvent, which may be, without limitation, a volatile silicone, ethanol, or a combination thereof; wherein the weight ratio of the first hydrophobic particulate material to the second hydrophobic particulate material is from about 1:10 to about 10:1; and wherein the aggregate weight percentage of all non-volatile liquid constituents in the composition is less than 10%, based on the entire weight of the composition.

The first hydrophobic particulate material is one which imparts superhydrophobicity to the surface by providing surface roughness in the nanometer scale. The first hydrophobic particulate material may comprise a hydrophobically surface-modified oxide, such as a metal oxide or a metalloid oxide, including for example, aluminum oxide, silicon dioxide, titanium dioxide, iron oxide, tin oxide, zinc oxide, zirconium dioxide, or combinations thereof. In the preferred practice of the invention, the first hydrophobic particulate material comprises hydrophobically-modified aluminum oxide such as that having the INCI name Trimethoxycaprylylsilane (and)

Alumina (International Cosmetic Ingredient Dictionary and Handbook, (2008) 12th Edition).

The second hydrophobic particulate material is one which, alone typically will not provide a superhydrophobic surface, but when used in combination with the first material preferably does not substantially negate the effect. The second hydrophobic particulate material provides the desirable tactile attribute of slip and eliminates or reduces the chalky feely left by the first hydrophobic particulate material on the hair. In various embodiments, the second hydrophobic particulate material may have a coefficient of dynamic friction less than 0.4, less than 0.3, less than 0.2, or ideally less than 0.1. The second hydrophobic particulate material may comprise substantially spherical particles of a polymer selected from the group consisting of polyethylene, polypropylene, polytetrafluoroethylene (PTFE), polyvinylchloride (PVC), polyvinyledenefluoride (PVDF), polyamide-imide, polymethylmethacrylate (PMMA), polyetheretherketone (PEEK), polyethylene terephthalate polyester (PETP), polystyrene, polydimethylsiloxanes, polymethylsisesquioxane, polyamide powder, Vinyl Dimethicone/Methicone Silsesquioxane Crosspolymer, silicone elastomer, Polysilicones, and combinations thereof. Polytetrafluoroethylene (PTFE), whether or not spherical, is a preferred second hydrophobic particulate material according to the invention. PTFE typically has a coefficient of dynamic friction of less than 0.05.

The second hydrophobic particulate material may also comprise lauroyl lysine, which may suitably be in the form of plate-shaped hexagonal crystals of N-lauroyl-L-lysine, ideally having a coefficient of dynamic friction of less than 0.1. Another preferred material is boron nitride.

The compositions may further comprise a shine enhancer, typically in an amount from 0.05 to 2.5% by weight of the total composition, to combat the matte finish produced by the first hydrophobic particulate material. In various embodiments, the shine enhancer is, without limitation, a hemispherical methyl methacrylate crosspolymer, or an aryl-silicone having a refractive index at 25° C. of greater than 1.4. Phenyltrimethicone is a non-limiting example of such an aryl silicone.

In a related embodiment, a composition for rendering a keratin fiber water-repellant is provided comprising: (a) from 0.1 to 5% by weight of a first hydrophobic particulate material comprising hydrophobically modified aluminum oxide; (b) from 0.1 to 5% by weight of a second hydrophobic particulate material, said second hydrophobic particulate material having a coefficient of dynamic friction less than 0.5; (c) from 90 to 99.8% by weight of a volatile solvent; wherein the weight ratio of the first hydrophobic particulate material to the second hydrophobic particulate material is from about 1:10 to about 10:1; and wherein the aggregate weight percentage of all non-volatile liquid constituents in the composition is less than 10%, based on the entire weight of the composition.

In another aspect of the invention, a method for rendering hair water-repellant is provided comprising applying thereto any of the inventive compositions and allowing the volatile solvents present to evaporate, thereby forming a superhydrophobic surface, preferably one which is characterized by a contact angle with a water droplet of at least 140°. The composition may be applied to wet hair or dry hair.

These and other aspects of the present invention will become apparent to those skilled in the art after a reading of the following detailed description of the invention, including the figures and appended claims.

DETAILED DESCRIPTION

As used herein, the term "superhydrophobic" refers generally to any surface which gives a contact angle with water of greater than about 140°. Superhydrophobicity can be quantitatively evaluated by measuring the contact angle with water using a contact angle goniometer or other like method known in the art or may be qualitatively evaluated by visual inspection and observation of water repellency, i.e., observation of water beads rolling off a cast film or by observing the weight of a hair sample before and after immersion in water.

All references to median or mean particle sizes herein are on a volume basis. All amounts provided in terms of weight percentage are relative to the entire composition unless otherwise stated. Unless otherwise provided, the term "alkyl" is intended to embrace straight-chained, branched, or cyclic hydrocarbons, particularly those having from one to 20 carbon atoms, and more particularly $C_{1-12}$ hydrocarbons.

As used herein, the term "keratin fiber" includes hair of the scalp, eyelashes, eyebrows, facial hair, and body hair such as hair of the arms, legs, etc. Keratin fibers are not limited to humans and also include any keratin fibers from a mammal, such as, for example, pet hair and mammalian fur.

The inventive cosmetic compositions for imparting superhydrophobicity to keratin fibers will generally be anhydrous, although water-containing formulations, such as water-in-oil emulsions are within the scope of the invention. As used herein, the water-in-oil emulsions include water-in-silicone emulsion. When reference is made to the weight % of a component based on the weight of the total composition, the total weight of the composition will be understood to include both the aqueous and oil phases of the emulsion. In the context of the present invention, water is considered a volatile solvent and will thus be excluded from the limitations on hydrophilic components and liquids described herein.

The compositions are preferably capable of providing a film on a keratin fiber, after evaporation of volatile solvents, which is characterized by a contact angle with a water droplet greater than about 140°, preferably greater than about 145°, and more preferred still, greater than about 150°. The contact angle is a measure of the hydrophobicity of the surface and is the angle at which a liquid/vapor interface meets a solid surface. Contact angles are suitably measured using a contact angle goniometer. In various embodiments, the contact angle with water will be about 140°, about 141°, about 142°, about 143°, about 144°, about 145°, about 146°, about 147°, about 148°, about 149°, or about 150°.

The compositions of the invention comprise a first particulate material and a second particulate material. The first particulate material comprises at least one hydrophobic particulate material which has a coefficient of dynamic (kinematic) friction, $\mu_k$, greater than 0.5. The second particulate material comprises at least one hydrophobic particulate material which has a coefficient of dynamic friction, $\mu_k$, less than 0.5. The first particulate material is often characterized by a chalky or gritty feel and may have substantially non-spherical shapes, whereas the second particulate material will typically comprise substantially spherical particles and will impart a smooth feeling on the hair. Without wishing to be bound by any theory, it is believed that the substantially non-spherical shape of the high $\mu_k$ (i.e., greater than 0.5) particles provides nano-scale roughness to the particles which is necessary for achieving superhydrophobicity. While not wishing to be bound by theory, it is thought that the particulate materials provide nano-scale (1 nm to ~1,000 nm) and/or micro-scale (1 μm to ~200 μm) surface roughness or structure on the hair surface, which imparts superhydrophobicity by providing protuberances on which water droplets may sit, thereby minimizing contact of the water with the surface at large, i.e., reducing surface adhesion. Surface roughness can be observed or measured by AFM, SEM, and the like. The high drag of the high $\mu_k$ particles also increases the substantivity of the particles against the hair, to the surprising extent that a binder is not essential to keep the particles on the hair. However, used alone or at high levels, such high particulate materials are largely incompatible with hair care products because they impart a chalky, gritty texture to the hair and provide a matte aesthetic and whitish color. However, in the inventive compositions, these drawbacks are surprisingly offset or mitigated by the inclusion of the second particulate materials having a coefficient of dynamic (kinematic) friction, $\mu_k$, less than 0.5. The second powdered material is typically one which by itself is not capable, or is less capable, of imparting a superhydrophobicity to hair. Unexpectedly, the superhydrophobicity of treated hair is not lost by the inclusion of the second particulate material in the inventive compositions.

The coefficient of dynamic friction may be suitably measured using, for example, a Friction Tester (KES-SE) manufactured by Kato Tech Co., LTD using a silicone rubber friction probe to measure a specific amount (e.g., 0.01 g) of sample evenly spread onto a ground quartz plate at a loaded weight of 50 g at 2 mm/sec.

The first particulate material, i.e., those hydrophobic particulates having a coefficient of dynamic (kinematic) friction, $\mu_k$, greater than 0.5, are typically, but not necessarily; substantially non-spherical in shape. These particulates may be based on oxide particles, such as metal oxide or metalloid oxide particles, which have been surface-treated to impart hydrophobic character. A preferred high dynamic friction particulate material according to the invention is surface-modified aluminum oxide ($Al_2O_3$). Hydrophobically modified silica ($SiO_2$) powder, including fumed silica or pyrogenic silica (e.g., having a primary particle size range from about 7 nm to about 40 nm and an aggregate particle size between about 100 and about 400 nm) is also contemplated to be particularly useful. Other notable particulate materials are hydrophobically modified metal oxides and metalloid oxides, including without limitation, titanium dioxide ($TiO_2$), iron oxides (FeO, $Fe_2O_3$, or $Fe_3O_4$), tin dioxide ($SnO_2$), zinc oxide (ZnO), zirconium dioxide ($ZrO_2$), and combinations thereof.

Hydrophobically modified particulates and methods for preparing hydrophobically modified particulates are well-known in the art, as described in, for example, U.S. Pat. No. 3,393,155 to Schutte et al., U.S. Pat. No. 2,705,206 to Wagner et al., U.S. Pat. No. 5,500,216 to Wagner et al., U.S. Pat. No. 6,683,126 to Keller et al., and U.S. Pat. No. 7,083,828 to Müller et al., U.S. Patent Pub. No. 2006/0110541 to Russell at al., and U.S. Patent Pub. No. 2006/0110542 to Dietz et al., the disclosures of which are hereby incorporated by reference. As used herein, a hydrophobically-modified particle is one which is rendered less hydrophilic or more hydrophobic by surface modification as compared to the particle in the absence of surface modification.

In one embodiment, a hydrophobic particle of the present invention may be an oxide particle having its surface covered with (e.g., covalently bound to) non-polar radicals, such as for example alkyl groups, silicones, siloxanes, alkylsiloxanes, organosiloxanes, fluorinated siloxanes, perfluorosiloxanes, organosilanes, alkylsilanes, fluorinated silanes, perfluorinated silanes and/or disilazanes and the like. The surface treatment may be any such treatment that makes the particles more hydrophobic. The surface of the particles may, for example, be covalently or ionically bound to an organic molecule or silicon-based molecule or may be adsorbed thereto, or the particle may be physically coated with a layer of hydrophobic material. There is essentially no limitation on the nature of the hydrophobic treatment and alkyl, aryl, or allyl silanes, silicones, dimethicone, fatty acids (e.g., stearates), polymeric silanes may be mentioned as well as fluoro and perfluoro derivatives thereof. The hydrophobic compound may be attached to the oxide particle through any suitable coupling agent, linker group, or functional group (e.g., silane, ester, ether, etc). The hydrophobic compound comprises a hydrophobic portion which may be selected from, for example, alkyl, aryl, allyl, vinyl, alkyl-aryl, aryl-alkyl, organosilicone, and fluoro- or perfluoro-derivatives thereof. Hydrophobic polymeric coatings including polyurethanes, epoxys and the like, are also contemplated to be useful. U.S. Pat. No. 6,315,990 to Farer, et al., the disclosure of which is hereby incorporated by reference, describes fluorosilane coated particulates which are formed by reacting a particulate having nucleophilic groups, such as oxygen or hydroxyl, with a silicon-containing compound having a hydrocarbyl group substituted by at least one fluorine atom and a reactive hydrocarbyloxy group capable of displacement by a nucleophile. An example of such a compound is tridecafluorooctyltriethoxy silane, available from Sivento, Piscataway, N.J., under the trade name DYNASILANE™ F 8261. Any of the hydrophobically modified particulate materials described in U.S. Pat. No. 6,683,126 to Keller et al., the disclosure of which is hereby incorporated by reference herein, are also contemplated to be useful, including without limitation those obtained by treating an oxide material (e.g., $SiO_2$, $TiO_2$, etc.) with a (perfluoro)alkyl-containing compound that contains at least one reactive functional group that undergoes a chemical reaction with the near-surface —OH groups of the oxide support particle, including for example hexamethyldisilazane, octyltrimethoxysilane, silicone oil, chlorotrimethylsilane, and dichlorodimethylsilane. A preferred hydrophobic coating according to the invention is prepared by treating an oxide, for example, alumina, with Trimethoxycaprylyl Silane.

In one particular preferred embodiment, the first particulate material is a fumed alumina or fumed silica which is surface-functionalized with alkylsilyl, fluoro-alkylsilyl, or perfluoro-alkylsilyl groups. Typically, the alkylsilyl groups will comprise $C_{1-20}$ hydrocarbons (more typically $C_{1-8}$ hydrocarbons) which are optionally fluorinated or perfluorinated. Such groups may be introduced by reacting at the particle surface silanes such as $C_{1-12}$-alkyl-trialkoxysilanes (e.g., $C_{1-12}$-alkyl-trimethoxysilanes or $C_{1-12}$-alkyl-triethoxysilanes). In another embodiment, the oxide particle has been surface treated with a fluoroalkylsilane, and in particular a perfluoroalkylsilane, such as a $C_{1-20}$ perfluoroalkylsilane, or more typically a $C_{1-12}$ perfluoroalkylsilane, including an exemplary embodiment wherein the iron oxide is surface-treated with a $C_8$ perfluoroalkylsilane. The pigments may be prepared by treating the oxide particle with a trialkoxyfluoroalkylsilane, such as Perfluorooctyl Triethoxysilane (INCI). Because the particles are preferably fumed (pyrogenic), the primary particle size will typically be very small, i.e., on the order of 5 nm to about 30 nm. The specific surface area of these particulate materials will typically, but not necessarily, range from about 50 to about 300 $m^2/g$, more typically, from about 75 to about 250 $m^2/g$, and preferably from about 100 to about 200 $m^2/g$.

Suitable hydrophobically modified fumed silica particles include, but are not limited to AEROSIL™ R 202, AEROSIL™ R 805, AEROSIL™ R 812, AEROSIL™ R 812 S, AEROSIL™ R 972, AEROSIL™ R 974, AEROSIL™ R 8200, AEROXIDE™ LE-1, AEROXIDE™ LE-2, and AEROXIDE™ LE-3 from Degussa Corporation of Parsippany, N.J. While silica ($SiO_2$) and hydrophobically-modified silicas are contemplated to be particularly useful in some embodiments, in other embodiments the compositions will be substantially free of silica or hydrophobically-modified silica. By substantially free of silica or hydrophobically-modified silica means that these components comprise less than about 2%, preferably less than about 1%, and more preferably less than about 0.5% by weight of the one or more particulate materials. A suitable hydrophobically modified alumina particulate is ALU C 805 from Evonik. The hydrophobically modified silica materials described in U.S. Patent Pub. 2006/0110542 to Dietz et al., incorporated herein by reference, are contemplated to be particularly suitable. In some embodiments, the compositions will be substantially free of alumina or hydrophobically modified alumina.

Suitable particulate materials having a coefficient of dynamic (kinematic) friction, $\mu_k$, greater than 0.5 include the octylsilanized fumed (pyrogenic) alumina, obtained by reacting trimethoxyoctylsilane with fumed alumina, which is sold under the name AEROXIDE™ ALU C805 by Evonik. That product is believed to have an average primary particle size of about 13 nm (nanometers) and a specific surface area (SSA) of about $100\pm15$ $m^2/g$. Other commercially available materials include, without limitation, AEROXIDE™ LE1, LE2, and LE3 by Evonik which are believed to be hydrophobic fumed silicas, surface-functionalized with alkylsilyl groups for hydrophobicity and a specific surface area (SSA) of about $160\pm30$ $m^2/g$, about $220\pm30$ $m^2/g$, and $100\pm30$ $m^2/g$, respectively.

The first particulate material will typically comprise a material having a $\mu_k$ value of 0.5 or above and will typically be up to about 0.6, about 0.7, about 0.8, or about 0.9. While it is believed that the octylsilanized fumed (pyrogenic) alumina sold under the trade name AEROXIDE™ ALU C805, referenced above, falls within these ranges, it will be understood that AEROXIDE™ ALU C805 is useful in the practice of the invention regardless of it s coefficient of dynamic friction. Accordingly, in one embodiment, the invention embraces a composition comprising AEROXIDE™ ALU C805 in combination with a second particulate material having a coefficient of dynamic friction of less than 0.5.

The first particulate materials will typically be in the form of a powder having a median particle size between about 1 nm (nanometers) and about 500 µm (micrometer), more typically between about 5 nm and about 200 µm preferably between about 7 nm and about 1 µm, 5 µm, 20 µm, 50 µm, or about 100 µm. Where the particulate material is employed is fumed (e.g., modified alumina and modified silica), the median particle size of the primary particles will typically be between about 5 nm and about 50 nm.

The first hydrophobic particulate material will comprise from about 0.01% to about 10% by weight of the composition, including volatile solvent, and more typically will comprise from about 0.1% to about 7.5%, and preferably from about 0.2% to about 5%, and more preferably, from about 0.5% to about 3%, and more preferred still from about 0.75% to about 1.5% by weight of the composition. In preferred embodiments, it has been found desirable not to exceed 3% by weight for the first hydrophobic particulate material, based on the entire weight of the composition (i.e., including solvent), for "normal" hair in order to prevent an excessively chalky look. By "normal" hair is meant hair that has not been damaged by chemical bleaching. For normal hair, it has been found optimal to include from 0.75 to 1.5% by weight of the first particulate material. However, for bleached or damaged hair, which is more hydrophilic than normal hair, it is possible, and desirable, to increase the amount of first particulate material above 3%, since more hydrophobic particulate material is needed to render the surface of the bleached hair superhydrophobic. Although increased hydrophobic particulate may render the hair lighter in appearance, on bleached hair this is not an issue because the effect is not noticeable as the hair is already very light in color.

The second particulate material is also hydrophobic in nature and is characterized by a low drag on hair by virtue of its low coefficient of dynamic friction. This imparts a tactile feeling of "slip" to the hair which counteracts or eliminates the chalky, gritty feeling of the first particulate material. The second particulate material will typically have a coefficient of dynamic friction less than 0.5. Such particulates often comprise substantially spherical or plate-shaped particles, whereas lumpy shaped particles tend to have higher $\mu_k$ values.

The second particulate material may comprise, for example, a hydrophobic organic powder. Suitable organic powders include, but are not limited, to spherical or substantially spherical polymeric particles of polyethylene, polypropylene, polytetrafluoroethylene (PTFE), polyvinylchloride (PVC), polyvinyledenefluoride (PVDF), polyamide imide, polymethylmethacrylate (PMMA), polyetheretherketone (PEEK), polyethylene terephthalate polyester (PETP), polystyrene, polydimethylsiloxanes, Polymethylsisesquioxane, polyamide (Nylon) powder, Vinyl Dimethicone/Methicone Silsesquioxane Crosspolymer, Polysilicones, and silicone elastomers, to name a few. Inorganic spherical particles include alumina and silica. By "substantially" spherical is meant that the shape of each particle is sufficiently spherical to provide a $\mu_k$ value less than 0.5. Silicone elastomers and PTFE may have a coefficient of dynamic friction less than 0.5 whether they are spherical or not. Other useful powders include fatty acid derivatives of lysine, notably N-lauroyl lysine (including L-lysine and D-lysine). N-lauroyl lysine is both water and oil insoluble and has a flat, hexagonal crystalline shape which provides a coefficient of dynamic friction of less than 0.1. Other useful platelet-shaped materials include talc, sericite, mica, and boron nitride.

Commercially available organic powders include, without limitation, methylsilsesquioxane resin microspheres, for example, TOSPEARL™ 145A, (Toshiba Silicone); particles of Polymethylsilsesquioxane sold under the name TOSPEARL™ 150 KA (Kobo); microspheres of polymethylmethacrylates, for example, MICROPEARL™ M 100 (Seppic); spherical particles of polymethylmethacrylate, such as those sold under the name TECHPOLYMER™ MB-8CA (KOBO); particles of VinylDimethicone/Methicone Silsesquioxane Crosspolymer sold under the name KSP™ 105 (ShinEtsu); the spherical particles of crosslinked polydimethylsiloxanes, for example, TREFIL™ E 506C or TREFIL™ E 505C (Dow Corning Toray Silicone); spherical particles of polyamide, for example, nylon-12, and ORGASOL™ 2002D Nat C05 (Atochem); polystyrene microspheres, for example Dyno Particles, sold under the name DYNOSPHERES™, and ethylene acrylate copolymer, sold under the name FLOBEAD™ EA209 (Kobo); aluminum starch octenylsuccinate, for example DRY FLO™ (National Starch); microspheres of polyethylene, for example MICROTHENE™ FN510-00 (Equistar), spherical particles of PTFE, available under the name FLUOROPURE™ 109 C (Shamrock) or MICROSLIP™ 519 (Presperse); silicone resin, polymethylsilsesquioxane silicone polymer, Polysilicones, including without limitation, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, and Polysilicone-19; Dimethicone/Divinyldimethicone/Silsesquioxane Crosspolymer (available under the trade name GRANSIL EPSQ from Grant Industries); dimethicone/silsesquioxane copolymer (available under the trade name SILDERM EPSQ from Active Concepts); platelet shaped powder made from N-lauroyl lysine, available under the name AMIHOPE™ LL (Ajinomoto), and mixtures thereof, to name a few. Other suitable particulates include the particulate silicon wax sold under the trade name TEGOTOP™ 105 (Degussa/Goldschmidt Chemical Corporation) and the particulate vinyl polymer sold under the name MINCOR™ 300 (BASF). Boron nitride is also contemplated to be suitable as a low coefficient of dynamic friction powder according to the invention.

In various embodiments of the invention, the second hydrophobic particulate material will have a coefficient of dynamic friction less than 0.5, less than 0.45, less than 0.4, The second particulate materials will typically be in the form of a powder having a median particle size between about 0.1 μm and about 500 μm, more typically between about 1 μm and about 200 μm (micrometer), preferably between about 1 μm and about 5 μm, 20 μm, 30 μm, 50 μm, or about 100 μm.

In other embodiments, either the first and/or second particulate materials according to the invention may be carbon, such as carbon black or graphite, provided that the coefficient of dynamic friction of the powder is appropriately selected. Suitable carbon black powders will typically have a mean particle size of about 0.01 μm to about 5 more typically between about 0.01 and about 1 μm, and preferably between about 0.01 and about 0.1 μm (i.e., about 10 to about 100 nanometers). The carbon black powder may have a surface area between about 50 and about 500 meters $(m)^2$/gram, more typically between about 100 and about 350 $m^2$/gram, and more typically between about 150 and about 300 $m^2$/gram as measured by nitrogen BET. A suitable carbon black is D&C Black No. 2 which is formed by the combustion of aromatic petroleum oil feedstock and consists essentially of pure carbon, formed as aggregated fine particles with a surface area range of 200 to 260 meters $(m)^2$/gram by nitrogen BET. D&C Black No. 2 is available from Sensient under the tradename Unipure black LC 902. This material has a mean particle size of about 0.04 μm.

The weight ratios of the first particulate material to the second particulate material in the compositions according to the invention are controlled to produce compositions with the desired balance between superhydrophobic effect and aesthetics. The first particulate material will typically be present at a weight ratio to the second particulate material of about 1:10 to about 10:1, or from about 1:5 to about 5:1, or from about 1:2 to about 2:1, including the ratio of about 1:2, about 1:1.75, about 1:1.5, about 1:1.25, about 1:1, about 1.25:1, about 1.5:1, about 1.75:1, and about 2:1. Particularly good results have been obtained where the weight ratio of the first particulate material to the second particulate material is about 1:1.

The first and second hydrophobic particulate materials will collectively comprise between about 0.01% to about 10% by weight of the composition, including volatile solvent, and more typically will comprise from about 0.1% to about 7.5%, and preferably from about 0.25% to about 5%, and more preferred still, from about 0.75% to about 2.5% by weight of the composition. Of course, it will be possible to prepare sprays and the like having a very low solids contents (e.g., between about 0.01% by weight and about 0.1% by weight), however, the composition will necessarily be sprayed or applied to the hair several times, allowing solvent to evaporate each time, in order to assure adequate coverage of the hair. Thus, the more preferred compositions will have higher solids contents in the range of, for example, 0.5% to about 10% by weight.

In various embodiments, the first hydrophobic particulate material will typically comprise from about 0.01% to about 10% by weight of the composition, including volatile solvent. In representative embodiments, the first hydrophobic particulate will comprise from about 0.1%, about 0.25%, about 0.5%, about 0.75%, about 1%, about 1.5%, about 2%, about 2.5%, about 3%, about 3.5%, about 4%, about 4.5%, or about 5% by weight of the total compositions (including volatile solvent).

The second hydrophobic particulate material will typically comprise from about 0.01% to about 10% by weight of the composition, including volatile solvent, and more typically will comprise from about 0.1% to about 7.5%, and preferably from about 0.2% to about 5%, and more preferably from about 0.5 to about 3% by weight of the composition. In various embodiments, the second hydrophobic particulate materials will comprise about 0.1%, about 0.25%, about 0.5%, about 0.75%, about 1%, about 1.5%, about 2%, about 2.5%, about 3%, about 3.5%, about 4%, about 4.5%, or about 5% by weight of the total compositions (including volatile solvent).

In some embodiments, it has been found desirable to include one or more agents that enhance the shine of hair treated with the compositions of the invention. The first hydrophobic particulate materials, particularly the hydrophobically-modified fumed oxides such as alumina and silica, impart a matte finish to the hair which may be undesirable from a consumers perspective. It has been discovered that shine can be restored to the hair, without sacrificing the water-repellency, by including one or more agents which modify the shine of hair. The shine-enhancing agent is preferably hydrophobic and is also preferably solid at room temperature such that the particulate material, particularly the first particulate material, does not become covered when the composition is applied to the hair. For example, lens-shaped particles such as hemi-spherical PMMA have been found suitable for imparting shine. One such commercially available material is a hemi-spherical methyl methacrylate crosspolymer sold under the trade name 3D Tech PW (Plain) XP (Kobo).

Silicone fluids, such as aryl-substituted siloxanes having high refractive indices are also useful as shine enhancers. Particular mention may be made of Phenyltrimethicone, which is available under the trade names SCI-TEC PTM 100 (ISP) and PDM20 (Wacker-Belsil). The PDM20 material has a refractive index of 1.437 at 25° C. In general, any aryl-substituted silicone having a refractive index of greater than 1.4 at 25° C. is contemplated to be suitable for restoring shine to hair treated with the inventive superhydrophobic materials. Another suitable silicone fluid that enhances shine is amodimethicone.

The shine enhancer is typically present from about 0.01% to about 5% by weight of the composition (including solvent). More typically, the shine enhancer component will comprise from about 0.05% to about 2.5% by weight of the composition. Preferably, the shine enhancer will comprise from about 0.1% to about 1.5% by weight of the composition, including embodiments wherein the shine enhancer is present at about 0.1%, 0.3%, 0.5%, 0.75%, 1%, 1.25%, or 1.5% by weight of the composition.

A film former is not necessary in the compositions because the first particulate material has been found to adequately adhere to the hair through static interactions alone. Thus, in some embodiments, the compositions will be free of film formers, such as polymeric film formers, waxes, oils, etc., or will be substantially free of film formers, by which is meant that the composition will comprise less than about 1% by weight film former, and preferably less than about 0.5% by weight film former, and more preferred still, less than about 0.1% by weight.

In other embodiments, a film-former may be included in the compositions. The film former preferably comprises a hydrophobic material. The hydrophobic film former may be any hydrophobic film former suitable for use in a cosmetic composition including, but not limited to, hydrophobic film-forming polymers. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. Alternatively, a "hydrophobic" film forming polymer may be said to be one which partitions preponderantly into the octanol phase when shaken with a mixture of equal volumes of water and octanol. By predominately is meant more the 50% by weight, but preferably more than 75% by weight, more preferably more than 95% by weight will partition into the octanol phase.

The film formers can be either natural or synthetic, polymeric or non polymeric, resins, binders, with low or high molar mass. Polymeric film formers can be either natural or synthetic, addition or condensation, homochain or heterochain, monodispersed or polydispersed, organic or inorganic, homopolymers or copolymers, linear or branched or crosslinked, charged or uncharged, thermoplastic or thermoset, elastomeric, crystalline or amorphous or both, isotactic or syndiotactic or atactic.

Polymeric film formers include polyolefins, polyvinyls, polyacrylates, polyurethanes, silicones, polyamides, polyesters, fluoropolymers, polyethers, polyacetates, polycarbonates, polyimides, rubbers, epoxies, formaldehyde resins, and homopolymers and copolymers of and of the foregoing.

Suitable hydrophobic (lipophilic) film-forming polymers include, without limitation, those described in U.S. Pat. No. 7,037,515 to Kalafsky, et al.; U.S. Pat. No. 6,685,952 to Ma et al.; U.S. Pat. No. 6,464,969 to De La Poterie, et al.; U.S. Pat. No. 6,264,933 to Bodelin, et al.; U.S. Pat. No. 6,683,126 to Keller et al.; and U.S. Pat. No. 5,911,980 to Samour, et al., the disclosures of which are hereby incorporated by reference.

Copolymers comprising one or more blocks selected from styrene (S), alkylstyrene (AS), ethylene/butylene (EB), ethylene/propylene (EP), butadiene (B), isoprene (I), acrylate (A) and methacrylate (MA), or a combination thereof, are contemplated to be suitable hydrophobic film formers. Particular mention is made of Ethylene/Propylene/Styrene and Butylene/Ethylene/Styrene copolymer including those sold under the trade name Versagel MD 1600 from Penreco as Gellants in IDD.

Special mention may be made of polyalkylenes, and in particular $C_2$-$C_{20}$ alkene copolymers, such as polybutene; alkylcelluloses with a linear or branched, saturated or unsaturated $C_1$-$C_8$ alkyl radical, such as ethylcellulose and propylcellulose; copolymers of vinylpyrrolidone (VP) and in particular copolymers of vinylpyrrolidone and of $C_2$ to $C_{40}$ and better still $C_3$ to $C_2$ alkene, including the copolymers of vinyl pyrollidone with eicosene or dodecane monomers sold under the tradenames Ganex V 220 and Ganex V 216 Polymers (ISP Inc. of Wayne, N.J.); silicone polymers and polyorganosiloxanes, including without limitations, polyalkyl siloxane, polyaryl siloxane, or a polyalkylaryl siloxane, with special mention being made of polydimethylsiloxanes; polyanhydride resins such as those available from Chevron under the trade name PA-18; copolymers derived from maleic anhydride and $C_3$ to $C_{40}$ alkenes such as octadecene-1; polyurethane polymers, such as Performa V 825 (New Phase Technologies) and those disclosed in U.S. Pat. No. 7,150,878 to Gonzalez, et al., incorporated by reference herein; and polymers and copolymers made from esters of vinylic acid monomers, including without limitation (meth)acrylic acid esters (also referred to as (meth)acrylates), for example, alkyl(meth)acrylates, wherein the alkyl group is chosen from linear, branched and cyclic ($C_1$-$C_{30}$) alkyls, such as, for example, ($C_1$-$C_{20}$) alkyl (meth)acrylates, and further still ($C_6$-$C_{10}$) alkyl(meth)acrylates. Among the alkyl(meth)acrylates which may be mentioned are those chosen from methyl methacrylate, ethyl methacrylate, butyl methacrylate, isobutyl methacrylate, 2-ethylhexyl methacrylate, lauryl methacrylate, and the like. Among the aryl(meth)acrylates which may be mentioned are those chosen from benzyl acrylates, phenyl acrylate, and the like. The alkyl group of the foregoing esters may be chosen, for example, from fluorinated and perfluorinated alkyl groups, that is to say that some or all of the hydrogen atoms of the alkyl group are replaced with fluorine atoms. Mention may also be made of amides of the acid monomers such as (meth)acrylamides, for example, N-alkyl(meth)acrylamides, such as ($C_1$-$C_{20}$) alkyls, including without limitation, N-ethylacrylamide, N-t-butylacrylamide, N-t-octylacrylamide and N-undecylacrylamide. Vinyl polymers for the hydrophobic film-forming polymer may also result from the homopolymerization or copolymerization of at least one monomer chosen from vinyl esters, olefins (including fluoroolefins), vinyl ethers, and styrene monomers. For example, these monomers may be copolymerized with at least one of acid monomers, esters thereof, and amides thereof, such as those mentioned above. Non-limiting examples of vinyl esters which may be mentioned are chosen from vinyl acetate, vinyl neodecanoate, vinyl pivalate, vinyl benzoate and vinyl t-butylbenzoate. Among the olefins which may be mentioned are those chosen, for example, from ethylene, propylene, butene, isobutene, octene, octadecene, and polyfluorinated olefins chosen, for example, from tetrafluoroethylene, vinylidene fluoride, hexafluoropropene and chlorotrifluoroethylene. Styrene monomers which may be mentioned are chosen, for example, from styrene and alpha-methylstyrene. The list of monomers given is not limiting, and it is possible to use any monomer known to those skilled in the art which falls within the categories of acrylic and vinyl monomers (including monomers modified with a silicone chain) which result in hydrophobic films. In this regard, particular mention may be made of the commercially available film formers Cyclopentasiloxane (and) Acrylates/Dimethicone Copolmer (KP-545, Shinetsu Chemical Co., Ltd).

Other film formers known in the art can be used advantageously in the composition. These include acrylate copolymers, acrylates $C_{12-22}$ alkyl methacrylate copolymer, acrylate/octylacrylamide copolymers, acrylate/VA copolymer, amodimethicone, AMP/acrylate copolymers, behenyl/isostearyl, butylated PVP, butyl ester of PVM/MA copolymers, calcium/sodium PVM/MA copolymers, dimethicone, dimethicone copolymers, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, $C_{30-38}$ olefin/isopropyl maleate/MA copolymer, hydrogenated styrene/butadiene copolymer, hydroxyethyl ethylcellulose, isobutylene/MA copolymer, methyl methacrylate crosspolymer, methylacryloyl ethyl betaine/acrylates copolymer, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyethylene, polymethyl methacrylate, polypropylene, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl PVP, trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

Additional non-limiting representatives of hydrophobic film-forming polymers include at least one polycondensate chosen from polyurethanes, polyurethane-acrylics, polyurethane-polyvinylpyrrolidones, polyester-polyurethanes, polyether-polyurethanes, polyureas and polyurea/polyurethanes. The polyurethanes may be for example, at least one chosen from aliphatic, cycloaliphatic, and aromatic polyurethanes, polyurealurethanes, and polyurea copolymers comprising at least one of: at least one sequence of at least one aliphatic The hydrophobic film may also be formed in situ by employing a resin which cures after application to the skin, nails, or hair, including for example, a polydimethylsiloxane film formed by in situ hydrosilation of a hydrosilane and an olefinic-substituted siloxane or by in situ polycondensation of alkoxy-functionalized siloxanes.

Preferred polymeric film formers include acrylates, alkyl acrylates, polyurethanes, fluoropolymers such as Fluomer (polyperfluoroperhydrophenanthrene) and silicone polymers. Particularly preferred are silicone acrylates such as acrylates/dimethicone copolymers sold under the trade names KP-545 or KP 550 (Shin-Etsu).

Other film formers that may be employed include, without limitation, natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax, and the like. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated). Commercially available ethylene-α-olefin copolymer waxes include those sold under the tradename PETROLITE® Copolymers (Baker Hughes Incorporated). Another wax that is suitable is dimethiconol beeswax available from Noveon as ULTRABEE™ dimethiconol ester.

Combinations of any of the foregoing film formers are also contemplated to be suitable, including combinations or polymeric and non-polymeric film formers.

The collective weight of the hydrophobic film formers, if present, will typically be between about 0.1% and about 5% by weight, more typically between about 0.1% and about 2.5%, or between about 0.5% and about 1.5% by weight, based on the total weight of the composition.

The compositions of the invention are typically, but not necessarily, provided as anhydrous or substantially anhydrous formulations. By "substantially anhydrous" is mean that the weight percentage of water in the composition is less than about 1%, preferably less than 0.5%, and most preferably less than about 0.1% by weight. Typically, the anhydrous compositions are substantially free of water by which is meant that water is not deliberately added to the compositions and the level of water is no more than would be expected based on the absorption of water from the air.

The compositions will typically comprise a volatile solvent. Volatile solvents may include volatile $C_{5-12}$ hydrocarbons, aromatic hydrocarbons (e.g., xylenes, toluene, etc.), ketones (e.g., actetone, methylethyl ketone, etc.), ethers (e.g., diethyl ether, methylethyl ether, etc.), perfluorohydrocarbons, hydrofluoroethers, freons, volatile silicones, lower alcohols, esters of acetic acid (e.g., ethylacetate, butylacetate, etc.) and the like. Preferred volatile solvents will be cosmetically acceptable, by which is meant that they are safe and non-irritating when applied to the body under conditions of normal use.

Volatile silicones are a preferred volatile solvent. By volatile silicone is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C. Volatile silicones include cyclic and linear volatile dimethylsiloxane silicones, including 0.5 cst dimethicone, 0.65 cst dimethicone, 1 cst dimethicone, and 1.5 cst dimethicone. In one embodiment, the volatile silicones may include cyclodimethicones, including tetramer (D4), pentamer (D5), and hexamer (D6) cyclomethicones, or mixtures thereof. Suitable dimethicones are available from Dow Corning under the name Dow Corning 200® Fluid and have viscosities ranging from 0.65 to 5 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics," Cosmetics and Toiletries, 91:27-32 (1976), herein incorporated by reference in its entirety. Linear volatile silicones generally have a viscosity of less than about centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as methyltrimethicone, trisiloxane, hexamethyldisiloxane, octamethyltrisiloxane, decamethyltetrasiloxane, and dodecamethylpentasiloxane to name a few.

Lower alcohol solvents, including methanol, ethanol, propanol, and isopropanol, are also contemplated to be useful. Ethanol is particularly preferred due to its high volatility and low toxicity. Preferably, the ethanol is anhydrous ethanol, such as SD Alcohol 40 from Exxon.

Among the volatile $C_{5-12}$ hydrocarbons, special mention may be made of isododecane which is available under the trade name Permethyl-99A (Presperse Inc.). Suitable fluorinated solvents include, without limitation, perfluoroethers, perfluorodecalin, perfluoromethyldecalin, perfluorohexane, perfluoromethylcyclohexane, perfluorodimethylcyclohexane, perfluoroheptane, perfluorooctane, perfluorononane, and perfluoromethylcycopentane, for example.

In a preferred embodiment, the solvent will comprise a combination of a volatile silicone, preferably cyclomethicone pentamer, and anhydrous ethanol. Preferably, the volatile silicone (cyclomethicone pentamer) will comprise from about 1% to about 99% and the ethanol will comprise from about 1% to about 99% by weight of the solvent system. More particularly, the volatile silicone (cyclomethicone pentamer) will comprise from about 50% to about 99% and the ethanol will comprise from about 1% to about 50% by weight of the solvent system. In a preferred embodiment, volatile silicone (cyclomethicone pentamer) will comprise from about 70% to about 90% and ethanol will comprise from about 10% to about 30% by weight of the solvent system.

In a further embodiment, the compositions according to the invention will comprise ethanol, preferably anhydrous, in combination with one or more solvents having a vapor pressure at 25° C. which is less than the vapor pressure of ethanol. In another embodiment, the compositions according to the invention will comprise ethanol, preferably anhydrous, in combination with one or more solvents having a vapor pressure at 25° C. which is greater than the vapor pressure of ethanol.

In addition to the foregoing, the compositions according to the invention may comprise additional pigments, pearlescents, and/or colorants combat the white appearance of fumed alumina or fumed silica or otherwise to impart a desired color to the hair, provided that such components do not undesirably detract from the superhydrophobic effect. Inorganic pigments include without limitation titanium dioxide, zinc oxide, iron oxides, chromium oxide, ferric blue, and mica; organic pigments include barium, strontium, calcium or aluminium lakes, ultramarines, and carbon black; colorants include without limitation D&C Green #3, D&C Yellow #5, and D&C Blue #1. Pigments and/or colorants may be coated or surface treated with one or more compatibilizers to aid in dispersion in the solvent. Preferred pigments and/or colorants are those surface treated to render them hydrophobic.

Preferred colorants include Iron Oxides, Black Oxide of Iron, Brown Iron Oxide, CI-77489, CI 77491, CI-77492, CI-77499, Iron Oxide Red 10-34-PC-2045, Pigment Black 11, Pigment Brown 6, Pigment Brown 7, Pigment Red 101, Pigment Red 102, Pigment Yellow 42, Pigment Yellow 43, Red Iron Oxide, Synthetic Iron Oxide, and Yellow Iron Oxide.

Various fillers and additional components may be added. Suitable fillers include without limitation silica, treated silica, talc, zinc stearate, mica, kaolin, Nylon powders such as Orgasol™, polyethylene powder, Teflon™, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The aggregate amount of all such additional pigments, colorants, and fillers is not particularly restricted provided that the superhydrophobicity of treated hair is not compromised. Typically, all additional pigments, colorants, fillers, etc., if present, will collectively comprise from about 0.1% to about 5% of the composition (including volatile solvent), but more typically will comprise from about 0.1% to about 1% or about 2% by weight of the composition.

The compositions of the invention may optionally comprise other active and inactive ingredients typically associated with cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. If present, the levels of such additional components should be judiciously selected so as not to adversely impact the ability of the emulsions to form superhydrophic films. Collectively, all such additional components suitably will comprise less than 5% by weight of the composition, but will typically comprise less than about 2% by weight, and will preferably will comprise less than 1% by weight, more preferably less than 0.5% by weight, and ideally less than 0.1% by weight of the total composition.

The compositions according to the invention will preferably comprise less than 10% by weight liquid components, other than volatile solvents, as it is believed that liquid components may cover the hydrophobically-modified oxides and consequently impair the hydrophobicity of the treated hair. In various embodiments, such components will comprise less than 5%, less than 4%, less than 3%, less than 2%, or less than 1% by weight, based on the total weight of the composition. In preferred embodiments, the compositions will comprise less than 0.5% by weight liquid components (other than volatile solvents), preferably less than 0.25% by weight, and more preferably less than 0.1% by weight liquid components. In other embodiments, the compositions will be free of liquid components other than volatile solvents.

In one embodiment, the composition will be free or substantially free of cationic hair conditioning agents. By substantially free of cationic hair conditioning agents is meant that the compositions comprise less than 0.5% by weight, preferably, less than 0.25% by weight, and more preferred still, less than 0.1% by weight cationic conditioning agents.

In other embodiments the compositions may contain an amount of cationic (quaternium) ingredients that are anhydrous or have very low level of water, e.g., less than 1% by weight. Suitable quaternium compounds include, without limitation, Cyclopentasiloxane and Silicone Quaternium-18 (INCI), PEG-2 Dimeadowfoamamidoethylmonium Methosulfate and Hexylene Glycol (INCI), and Cetrimonium Chloride (INCI), to name a few. Such quaternium compounds, if present, will typically comprise from about 0.05% to about 1.5% by weight of the total composition, and more typically, from about 0.1% to about 1% by weight.

Particularly deleterious to the realization of superhydrophobicity are non-volatile water-soluble or water-dispersible components which may coat or mask the particulates on the surface of the hair. Preferably, the collective amount of such non-volatile water-soluble or water-dispersible components in the composition will be below about 10%, below about 5%, below about 2.5%, below about 1%, below about 0.5%, below about 0.25%, below about 0.1%, or below about 0.05%, based on the total weight of the composition (including volatile solvent). In some embodiments, the compositions are free of non-volatile water-soluble or water-dispersible components, and in particular, free of liquid water-soluble or water-dispersible components.

The first particulate material may comprise, consist essentially of, or consist of a particular hydrophobically modified oxide, such as for example, octylsilyl-functionalized fumed alumina. By "consist essentially of" a particular hydrophobically modified oxide (e.g., octylsilyl-functionalized fumed alumina) is meant that the presence of additional hydrophobic particulates having a coefficient of dynamic friction greater than 0.5 is excluded to the extent that the presence of such additional hydrophobic particulates would have a measurable impact on superhydrophobicity or aesthetic (color, feel, shine, etc.) when applied to the hair. In some embodiments, the first particulate component may comprise more than about 5%, more than about 10%, more than about 15%, more than about 20%, more than about 25%, more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, or more than about 95% by weight of a particular hydrophobically-modified oxide, such as octylsilyl-functionalized fumed alumina.

The compositions are ideally intended for pump or aerosol delivery to the hair. When formulated for aerosol delivery, a propellant will be included which is suitable for delivery of the composition onto the hair. Suitable propellants include, without limitation, n-butane, isobutane, and isobutane/propane, nitrogen, carbon dioxide, compressed air, nitrous oxide, 1,2-difluoroethane, 1,1-difluoroethane, 1,1,1,2-tetrafluoroethane, dimethyl ether, and mixtures thereof. When reference is made to the total weight of the inventive compositions herein, such weight will be understood to exclude the weight of the propellant.

In one embodiment, a product is provided comprising an aerosol device including a container fitted with an dispenser, such as a dispensing valve, for dispensing the aerosol composition from the container. The container is charged with the composition according to the invention (e.g., comprising a first particulate material, a second particulate material, and volatile solvent). A suitable propellant may be included in the container with the inventive composition or may be included in a second container in a dual-chamber-type aerosol device. When the propellant is included in the container with the other ingredients, it will typically be present from about 20% to about 50%, by weight of the composition including propellant.

The compositions of the invention may suitably be prepared by mixing the solvent (e.g., ethanol and cyclomethicone pentamer) with the particulate materials and, if present, the shine enhancer and optional ingredients. There is essentially no restriction on the order of addition or manner of mixing these components. The composition may be mixed or homogenized at room temperature. It has been found useful but not necessary to mill the mixed ingredients which can be carried out using any suitable technique in the art. For example, a Silversen L4RT mixer operating at 4000 RPM for about 4 minutes has been found suitable and is the method used to prepare compositions according to the Examples. Once complete, the composition can be packaged, for example into a pump spray, or an aerosol spray which is then charged with propellant.

The compositions according to the invention are preferably applied to the hair (hair of the body, scalp, beard, mustache, eyelashes, etc.) to provide resistance against wetting. Thus, for example, the composition may be applied to the hair before swimming such that the hair does not become wet, or becomes only minimally wet, after submersion in water. By minimally wet is meant that the weight of the hair after submersion is increased by 20% or less, preferably by 15% or less, more preferably by 10% or less, and more preferred still by 7.5% or less, as compared to the weight of the hair prior to submersion in water. Further, after one or two vigorous shakes of the hair, the hair will be essentially dry. By essentially dry is meant that the weight of the hair will be increased by less than about 5% or less than about 2.5% as compared to the weight of the hair before submersion. The foregoing May be tested using hair swatches treated with the inventive compositions. Likewise, the compositions may be applied to the hair of a pet, such as a dog, before swimming such that the pet is substantially dry immediately after swimming without the need for toweling off, etc., or to livestock so they are not wetted by snow, rain or mud.

The inventive composition may be applied, preferably sprayed, onto dry hair or wet hair. It has surprisingly been found the superhydrophobicity may be achieved even in the case where the composition is applied to wet hair.

It has surprisingly been found that the compositions may provide the dual benefits of increasing water repellency and improving the volume of the hair when applied substantially uniformly to the hair of the head. The volume may be increased by at least about 20%, at least about 50%, at least about 75%, or even at least about 100%. The increase in volume may suitably be determined on hair tresses using the technique described by C. R. Robbins and R. J. Crawford in the article "A Method to Evaluate Hair Body," *J. Soc. Cosmet. Chem.*, 35, pp. 369-377 (1984), the disclosure of which is hereby incorporated by reference herein.

Additional components may be incorporated as fillers or for various functional purposes as is customary in the art. However, while additional components consistent to formulate the above cosmetic compositions may be included, the inclusion of additional ingredients is limited to those ingredients which do not interfere with the formation of a superhydrophobic surface on the hair.

EXAMPLES

The examples below illustrate the effects on water-repellency, feel, and shine of hair from application of various compositions comprising high dynamic friction hydrophobic particulate materials and low dynamic friction hydrophobic particulate materials, individually or in combination.

The high dynamic friction (e.g., ≥0.5) particulate materials in the examples provided below are (i) AEROXIDE™ ALU C805 by Evonik, which is Trimethoxycaprylylsilane (and) Alumina (INCI), an octylsilanized fumed (pyrogenic) alumina obtained by reacting trimethoxyoctylsilane with fumed alumina and (ii) a titanium dioxide/aluminum hydroxide/methicone/hydrated silica sold under the designation SMT-100SAS.

The low dynamic friction (e.g., <0.5) in the following examples is either (i) a vinyl dimethicone/methicone silsesquioxane crosspolymer sold under the designation KSP-105 by Shin-Etsu Chemical Co., Ltd., (ii) a powdered polytetrafluoroethylene (PTFE) sold under the designation FLUOROPURE™ 109C by Shamrock Technologies Inc., or (iii) a lauroyl lysine powder sold under the designation AMIHOPE™ LL by Ajinomoto.

The volatile solvents comprise anhydrous ethyl alcohol (Alcohol SD 40B Anhydrous) and cyclopentasiloxane (cyclomethicone pentamer), which is available under the designation Dow Corning 245® Fluid.

Example I

The effect of adding a high dynamic friction particulate material in combination with a second particulate material was investigated in relation to the hydrophobicity, tactile feel and appearance of treated hair. Eleven samples (1-11) of a cosmetic composition were prepared according to Table 4 below. The hydrophobicity, tactile feel and appearance of hair samples treated with the cosmetic compositions of Table 4 were examined. The testing protocol is described below.

Hydrophocity, Tactile Feel and Appearance Test Method

The composition to be evaluated was sprayed onto a hair swath weighing approximately 5-12 g. The volatile solvents from the cosmetic composition were allowed to evaporate until dry. An initial weight of the treated hair sample is obtained and the tactile feel and appearance of the cosmetic composition is assessed on the basis of a scale shown below in Table 1.

TABLE 1

| Scale | Assessment of Tactile Feel and Appearance |
|---|---|
| 1 | Soft, natural feel, no residue or gritty feel, and no white residues on the hair |
| 2 | Soft, but some residue or gritty feel, and no white residues on the hair |
| 3 | Soft, but some residue or gritty feel, and some white residues on the hair |
| 4 | Some drag, lots of residue or gritty feel, and no white residues on the hair |

TABLE 1-continued

| Scale | Assessment of Tactile Feel and Appearance |
|---|---|
| 5 | A lot of drag, gritty, dry, and no white residues on the hair |
| 6 | A lot of drag, gritty, dry and some white residues on the hair |
| 7 | Worst feel, gritty, dry, and substantial amount of white residues on the hair. |

The treated hair sample is also visually evaluated for its shine. The shine of the treated hair sample is quantified on the basis of the Star Grading System as shown below in Table 2.

TABLE 2

| Star Grading System | |
|---|---|
| Scale | Visual Assessment of Shine |
| * (1) | Matte |
| ** (2) | No Shine |
| *** (3) | Small Amounts of Perceivable Shine |
| **** (4) | Medium Shine |
| ***** (5) | High Shine |

The treated hair sample is then immersed in water and subsequently removed from the water. The hydrophobicity of the sample is visually assessed and the weight of tested hair sample is obtained. The hydrophobicity of the tested sample is visually evaluated by observing whether water droplets remain on the hair sample, and if so, whether the water can be removed with or without shaking the hair sample. The result is recorded using a Letter Grading System as shown below in Table 3.

TABLE 3

| Letter Grading System | |
|---|---|
| Scale | Visual Assessment of Hydrophobicity |
| A | Excellent Waterproofing, no shaking required. |
| B | Good Hydrophobicity, only a few drops on sample |
| C | Good Hydrophobicity, only a few drops on sample, but requires some shaking |
| D | Needs excessive shaking in order for water to roll off. |
| E | Poor Hydrophobicity |

The results of these tests for Samples 1-11, including a quantitative determination of the amount of water remaining on the hair, are shown below in Table 4.

TABLE 4

| | Sample Number: | | | | | | | | | | |
|---|---|---|---|---|---|---|---|---|---|---|---|
| | 1 | 2 | 3 | 4 | 5 | 6 | 7 | 8 | 9 | 10 | 11 |
| Component | Weight % | | | | | | | | | | |
| AEROXIDE ™ ALU C805 | 0.75 | — | — | — | 0.75 | 0.75 | 0.75 | 0.75 | — | — | — |
| KSP-105 | — | — | — | 0.75 | — | — | 0.75 | — | 0.75 | 0.75 | — |
| SMT-100SAS | — | — | — | — | 0.75 | — | — | — | — | — | — |
| FLUOROPURE ™ 109C | — | 0.75 | — | — | — | 0.75 | — | — | 0.75 | — | 0.75 |
| AMIHOPE ™ LL | — | — | 0.75 | — | — | — | — | 0.75 | — | 0.75 | 0.75 |
| Alcohol SD 40B Anhydrous | 22 | 22 | 22 | 22 | 22 | 22 | 22 | 22 | 22 | 22 | 22 |

TABLE 4-continued

| Component | Sample Number: | | | | | | | | | | |
|---|---|---|---|---|---|---|---|---|---|---|---|
| | 1 | 2 | 3 | 4 | 5 | 6 | 7 | 8 | 9 | 10 | 11 |
| | Weight % | | | | | | | | | | |
| Dow Corning 245 ® Fluid | q.s. | q.s. | q.s. | q.s. | q.s. | q.s. | q.s. | q.s. | q.s. | q.s. | q.s. |
| Total: | 100 | 100 | 100 | 100 | 100 | 100 | 100 | 100 | 100 | 100 | 100 |
| weight % water remaining | 1.35 | 9.18 | 21.16 | 15.17 | 5.36 | 2.06 | 7.12 | 13.34 | 17.29 | 33.49 | 17.24 |
| Water repellency | A | C | D | C | A | A | B | C | D | E | D |
| Feel and Appearance | 4 | 1 | 1 | 2 | 5 | 2 | 2 | 2 | 1 | 1 | 1 |
| Shine | *** | **** | **** | **** | ** | **** | *** | *** | **** | **** | **** |

The results indicate that, AEROXIDE™ ALU C805 (Sample 1) imparts superior water repellency (having a Letter Grading of A) as compared to samples having only low dynamic friction particulate materials (Samples 2-4). However, AEROXIDE™ ALU C805 alone in a cosmetic composition (Sample 1) imparts undesirable drag and lack of shine to the hair. Although the low dynamic friction particulate materials (Samples 2-4) provide poor hydrophobic properties, these materials impart soft tactile properties, a natural appearance, and acceptable shine to the hair.

It was observed that the combination of a high dynamic friction particulate material such as AEROXIDE™ ALU C805 with a low coefficient of dynamic friction hydrophobic particulate material (Samples 6-8) imparts balanced properties suitable for application to the hair. In contrast, a cosmetic composition having a combination of two high coefficient of dynamic friction particulate materials (Sample 5) exhibited unacceptable drag and undesirable residue or gritty feel, whereas combinations of two low coefficient of dynamic friction particulate materials (Samples 9-11) provided a soft tactile feel and superior shine, but were significantly inferior in water repellency.

Example II

Samples 12 through 18, as shown in Table 5 below, were prepared to investigate the effect of different ratios of AEROXIDE™ ALU C805 (high $\mu_k$) and KSP-105 (low $\mu_k$) on the hydrophobicity, tactile feel and appearance of treated hair swaths using the method described in Example I. The results of these tests are provided in Table 5.

TABLE 5

| Component | Sample Number: | | | | | | |
|---|---|---|---|---|---|---|---|
| | 12 | 13 | 14 | 15 | 16 | 17 | 18 |
| | Weight % | | | | | | |
| AEROXIDE ™ ALU C805 | 0.5 | 0.75 | 1 | 0.75 | 0.75 | 0.75 | 0.75 |
| KSP-105 | 1 | 0.75 | 0.5 | 0 | 0.5 | 0.75 | 1 |
| Alcohol SD 40B Anhydrous | 22 | 22 | 22 | 22 | 22 | 22 | 22 |
| Dow Corning 245 ® Fluid | q.s. | q.s. | q.s. | q.s. | q.s. | q.s. | q.s. |
| Total: | 100 | 100 | 100 | 100 | 100 | 100 | 100 |
| weight % water remaining | 15.50 | 5.73 | 1.98 | 1.35 | 0.30 | 7.12 | 9.04 |
| Water repellency | D | B | A | A | A | B | B |
| Feel and Appearance | 2 | 2 | 2 | 4 | 2 | 2 | 2 |
| Shine | *** | *** | *** | *** | *** | *** | *** |

As the ratio of AEROXIDE™ ALU C805 to KSP-105 varied from 1:2 (Sample 12) to 2:1 (Sample 14), the hydrophobicity improved from a "D" rating at a ratio of 1:2 to an "A" rating at a ratio of 2:1. Consistent with the results for Samples 12 through 14, as the amount of KSP-105 increased from 0 to 1 weight % at a constant weight of AEROXIDE™ ALU C805 (Samples 15-18), water repellency diminished. This is likely due to the fact that the Vinyl Dimethicone/Methicone Silsesquioxane Crosspolymer (INCI) material begins to coat the alumina particles at higher loadings and thereby reduce the nano-structured surface available for interaction with water droplets. However, in Samples 12-14 and 16-18 the presence of KSP-105 significantly improved the tactile feel and appearance of the cosmetic composition as compared to Sample 15.

Notably, Sample 16 exhibits excellent water repellency, achieving a grade of "A," and provides a suitable tactile feel and appearance grading of 2.

Example III

Samples 19 through 23 were prepared to investigate the effect of different loadings of the combination of AEROXIDE™ ALU C805 and KSP-105 (the same high and low coefficient of dynamic friction hydrophobic particulate materials employed in Example I) on the hydrophobicity, tactile feel and appearance of hair treated with the composition. Samples 19 through 23 were prepared according to Table 6 and the hydrophobicity, tactile feel and appearance, and shine were determined using the method described in Example I.

TABLE 6

| Component | Sample Number: | | | | |
|---|---|---|---|---|---|
| | 19 | 20 | 21 | 22 | 23 |
| | Weight % | | | | |
| AEROXIDE ™ ALU C805 | 0.75 | 1.5 | 3 | 5 | 10 |
| KSP-105 | 0.75 | 1.5 | 3 | 5 | 10 |
| Alcohol SD 40B Anhydrous | 22 | 22 | 22 | 22 | 22 |
| Dow Corning 245 ® Fluid | q.s. | q.s. | q.s. | q.s. | q.s. |
| Total: | 100 | 100 | 100 | 100 | 100 |
| weight % water remaining | 5.73 | 6.88 | 0.27 | 0.00 | 0.88 |
| Water repellency | B | B | A | A | A |
| Feel and Appearance | 2 | 4 | 3 | 6 | 6 |
| Shine | *** | *** | * | * | * |

The results indicate that as the total amount of the AEROXIDE™ ALU C805 and KSP-105 combination increased, the water repellency improved from a "B" to an "A." However, as the hydrophobic property improved, the look and feel attributes were compromised. Specifically, where AEROXIDE™ ALU C805 and KSP-105 each comprise at least 3 weight % of the cosmetic composition (Samples 21 to 23), the cosmetic composition was matte and a white residues was visible. Below 3 weight % for each component, water repellency was acceptable and the shine was improved. Sample 19, which comprises 0.75 weight % of AEROXIDE™ ALU C805 and 0.75 weight % of KSP-105, demonstrated excellent balance between water repellency, tactile feel, appearance, and shine.

Example IV

This example provides a composition according to the invention which is suited for application to bleached or damaged hair. The composition has the ingredients shown in Table 7.

TABLE 7

| Ingredient | weight % |
|---|---|
| cyclomethicone pentamer | 72.8 |
| anhydrous ethanol | 20 |
| Trimethoxycaprylylsilane (and) Alumina | 2.5 |
| Polymethyl Methacrylate Spherical | 0.1 |
| Methyl Methacrylate Crosspolymer | 0.1 |
| VinylDimethicone/Methicone Silsesquioxane Crosspolymer | 4.5 |
| Water repellency | A |
| Feel and Appearance | 2 |
| Shine | **** |

The low coefficient of dynamic friction particulate material used in this example includes (i) the VinylDimethicone/Methicone Silsesquioxane Crosspolymer sold as KSP 105 by Kobo, and (ii) a spherical polymethyl methacrylate which is commercially available from Kobo under the designation Techpolymer MB-8CA. The Methyl Methacrylate Crosspolymer is a shine enhancing ingredient which has a hemispherical shape. It is available from Presperse under the designation 3D Tech PW (Plain) XP.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A method for rendering keratin fiber water-repellant comprising applying thereto a composition comprising:
   (a) a first hydrophobic particulate material, wherein the first hydrophobic particulate material consisting of octylsilyl-functionalized fumed alumina;
   (b) a second hydrophobic particulate material having a coefficient of dynamic friction less than 0.5 wherein said second hydrophobic particulate material comprises substantially spherical particles of a polymer selected from the group consisting of polyethylene, polypropylene, polytetrafluoroethylene (PTFE), polyvinylchloride (PVC), polyvinyledenefluoride (PVDF), polyamide-imide, polymethylmethacrylate (PMMA), polyetheretherketone (PEEK), polyethylene terephthalate polyester (PETP), polystyrene, polydimethylsiloxanes, polymethylsilsesquioxane, polyamide powder, Vinyl Dimethicone/Methicone Silsesquioxane Crosspolymer, silicone elastomer, Polysilicones, and combinations thereof;
   (c) optionally, one or more of: (i) a shine enhancing agent, (ii) a hydrophobic film former, (iii) non-volatile liquid constituents, (iv) a filler, (v) a cationic hair conditioning agent, and (vi) other active and inactive ingredients; and
   (d) a volatile solvent;
   wherein said first and second hydrophobic particulate materials collectively are from about 0.01% to about 10% by weight, based on the entire weight of the composition; and wherein a weight ratio of said first hydrophobic particulate material to said second hydrophobic particulate material is from about 1:10 to about 10:1; and wherein an aggregate weight percentage of all non-volatile liquid constituents in said composition is less than 10%, based on the entire weight of the composition; and allowing the volatile solvent present to evaporate.

2. A method for rendering keratin fiber water-repellant comprising applying thereto a composition comprising:
   (a) a first hydrophobic particulate material, wherein the first hydrophobic particulate material consisting of octylsilyl-functionalized fumed alumina;
   (b) a second hydrophobic particulate material having a coefficient of dynamic friction less than 0.5 wherein the second hydrophobic particulate material is VinylDimethicone/Methicone Silsesquioxane Crosspolymer (INCI);
   (c) optionally, one or more of: (i) a shine enhancing agent, (ii) a hydrophobic film former, (iii) non-volatile liquid constituents, (iv) a filler, (v) a cationic hair conditioning agent, and (vi) other active and inactive ingredients; and
   (d) a volatile solvent;
   wherein said first and second hydrophobic particulate materials collectively are from about 0.01% to about 10% by weight, based on the entire weight of the composition; and wherein a weight ratio of said first hydrophobic particulate material to said second hydrophobic particulate material is from about 1:10 to about 10:1; and wherein an aggregate weight percentage of all non-volatile liquid constituents in said composition is less than 10%, based on the entire weight of the composition; and allowing the volatile solvent present to evaporate.

3. The method according to claim 1, wherein the volatile solvent is present in an amount of from 90% to 99.8%.

4. The method according to claim 1, wherein the film former is present in an amount of from about 0.1% to about 5% by weight.

5. The method according to claim 1, wherein the conditioning agent is present in an amount of from about 0.05% to about 1.5% by weight.

6. The method according to claim 1, wherein the non-volatile liquid constituents are present in an amount of less than about 2% by weight.

7. The method according to claim 1, wherein the shine enhancing agent is present in an amount of less than about 5% by weight.

8. The method according to claim 1, wherein said volatile solvent comprises a volatile silicone.

9. The method according to claim 8, wherein the volatile solvent comprises water and is a water-in-oil emulsion.

10. The method according to claim 1, wherein said first and second hydrophobic particulate materials collectively are from about 0.1% to about 5% by weight of said composition.

11. The method according to claim 1, wherein the weight ratio of the first hydrophobic particulate material to the second hydrophobic particulate material is from about 1:5 to about 2:1.

12. The method according to claim 1, wherein the cationic conditioning agent is present in an amount of from about 0.05% to about 0.5% by weight, wherein the non-volatile liquid constituents are present in an amount of less than about 2% by weight, and wherein the shine enhancing agent is present in an amount of less than about 5% by weight.

13. The method according to claim 12, wherein the volatile solvent is present in an amount of from 90% to 99.8% by weight.

14. The method according to claim 13, wherein the film former is present in the composition in an amount of from about 0.1% to about 5% by weight.

15. The method according to claim 1, wherein said second hydrophobic particulate material is VinylDimethicone/Methicone Silsesquioxane Crosspolymer (INCI).

16. The method according to claim 2, wherein the volatile solvent is present in an amount of from 90% to 99.8%.

17. The method according to claim 16, wherein said second hydrophobic particulate material has a coefficient of dynamic friction less than 0.3.

18. The method according to claim 2, wherein the film former is present in an amount of from about 0.1% to about 5% by weight.

19. The method according to claim 2, wherein the cationic conditioning agent is present in an amount of from about 0.05% to about 0.5% by weight.

20. The method according to claim 2, wherein the non-volatile liquid constituents are present in an amount of less than about 2% by weight.

21. The method according to claim 2, wherein the shine enhancing agent is present in an amount of less than about 5% by weight.

22. The method according to claim 2, wherein said volatile solvent comprises a volatile silicone.

23. The method according to claim 22, wherein the volatile solvent comprises water and is a water-in-oil emulsion.

24. The method according to claim 2, wherein said first and second hydrophobic particulate materials collectively are from about 0.1% to about 5% by weight of said composition.

25. The method according to claim 2, wherein the weight ratio of the first hydrophobic particulate material to the second hydrophobic particulate material is from about 1:5 to about 2:1.

26. The method according to claim 2, wherein the cationic conditioning agent is present in an amount of from about 0.05% to about 0.5% by weight, wherein the non-volatile liquid constituents are present in an amount of less than about 2% by weight, and wherein the shine enhancing agent is present in an amount of less than about 5% by weight.

27. The method according to claim 26, wherein the volatile solvent is present in an amount of from 90% to 99.8% by weight.

28. The method according to claim 27, wherein the film former is present in the composition in an amount of from about 0.1% to about 5% by weight.

* * * * *